United States Patent [19]

Keeler et al.

[11] Patent Number: 5,378,820
[45] Date of Patent: Jan. 3, 1995

[54] GENE ENCODING CYTADHESIN PROTEIN OF MYCOPLASMA GALLISEPTICUM AND ITS USE

[76] Inventors: Calvin L. Keeler, 1320 Barksdale Rd.; John E. Dohms, 126 E. Cleveland Ave., both of Newark, Del. 19711

[21] Appl. No.: 973,257

[22] Filed: Nov. 9, 1992

[51] Int. Cl.$^6$ ............... C07H 21/02; C07H 17/00; C12N 15/00; C12N 1/20
[52] U.S. Cl. ............... 536/23.1; 536/24.3; 536/18.7; 536/24.32; 435/6; 435/7.2; 435/69.1; 435/172.3; 435/252.3; 435/320.1; 435/870
[58] Field of Search ............ 435/6, 7.1, 7.9, 7.32, 435/7.92, 7.95, 29, 7.2, 91.1, 69.1, 172.3, 252.3, 870, 320.1; 436/501, 518; 530/387.1; 536/18.7, 23.1, 24.3, 24.32

[56] References Cited

U.S. PATENT DOCUMENTS 5,026,636  6/1991  Baseman et al. .................. 435/6
5,158,870  10/1992  Baseman et al. ............... 435/7.32

OTHER PUBLICATIONS

Hu et al. Is J. of Mecl. Sc. 20:916 (1984).
Dallo et al., Microbial Pathogenesis 8:371 (1990).
Dallo et al., Inf. & Imm. 57:1059 (1989).
Dohms et al., Cloning of the Mycoplasma Gallisepticum Cytadhesion Gene, Abstract of paper presented at the Conference of Research Worker on Animal Diseases on Nov. 11–12, 1991.
Inamine et al., Gene 73:175 (1988).
Inamine et al., Gene 82:259 (1989).
Kahn et al., Avian pathology 18:135 (1989).
Su et al., Inf. & Imm. 55:3023 (1987).

*Primary Examiner*—Margaret Parr
*Assistant Examiner*—Miguel Escallon
*Attorney, Agent, or Firm*—Connolly & Hutz

[57] ABSTRACT

The nucleic acid encoding the membrane-associated cytadhesin protein of *M. gallisepticum* is disclosed, together with the amino acid sequence of the encoded product. The nucleic acid sequence finds utility as a probe for *M. gallisepticum* DNA to diagnose *M. gallisepticum* infection in poultry. Expression of fragments of the nucleic acid sequence into polypeptide is also disclosed.

6 Claims, 4 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
  ( A ) LENGTH: 4182 base pairs
  ( B ) TYPE: Nucleic Acid
  ( C ) STRANDEDNESS: double stranded
  ( D ) TOPOLOGY: linear ( i i ) MOLECULE TYPE: Genomic DNA ( i i i ) HYPOTHETICAL: No ( i v ) ANTI-SENSE: No ( v i ) ORIGINAL SOURCE:
  ( A ) ORGANISM: Mycoplasma Gallisepticum
  ( B ) STRAIN: S6

( x i ) SEQUENCE DESCRIPTION: SEQ ID NO: 1:

```
CTGCAGCAGT  GCCAACTGAA  GAAGTTAATA  CTCAAGAACC  AACTCAACCA         50

GCTGGTGTTA  ATGTAGCTAA  TAACCCTCAG  ATGGGGATCA  ATCAACCAGG        100

ATTTAATCAA  CCTCAGATTA  ATCCGCAATT  TGGTCCTAAT  CCCCAACAAA        150

GAATTAACCC  ACAGGGCTTT  GGTGGCCCAA  TGCCACCTAA  CCAAATGGGA        200

ATGCGACCAG  GGTTTAACCA  AATGCCCCCA  CAAATGGGAG  AATGCCACC         250

TAACCAAATG  GGAATGCGAC  CAGGGTTTAA  CCAAATGCCC  CCACAAATGG        300

GAGGAATGCC  ACCAAGACCA  AACTTCCCTA  ACCAAATGCC  TAATATGAAT        350

CAACCAAGAC  CAGGTTTCAG  ACCACAACCT  GGTGGTGGGG  TGCCGATGGG        400

AAATAAAGCT  GTAGGTGGGT  TTAATCACCC  AGGTGCACCA  ATGGGTCCAA        450
```

| | | | | | | | | | | |
|---|---|---|---|---|---|---|---|---|---|---|
| ACCGCATGAA | CTTCCCTAAT | CAAGGAATGA | ATCAACCCCC | ATACATGGCA | | | | | | 500 |
| GGACCAAGAG | CTGGTTTTCC | ACCGCAAAAT | GGACCTAGAT | AAGACTTTAG | | | | | | 550 |
| AAAACTAAAA | CTTAATCTTT | ATCAACTAAA | AAAAGATATT | TAAACCAAAA | | | | | | 600 |
| ATATTATTAT | TAAATCTTAT | TAAATCTTAT | TAAACTTTTT | ATATATTTAT | | | | | | 650 |
| ATAACAAGAA | TCAAATCTTT | GAATAACCTA | ATATTTGTTA | ACATAGTAAA | | | | | | 700 |

```
AGAATTTAGA TC GTG AAA AAA CTT ATT TTT AAA TTA TCA GTC GGA        745
              Val Lys Lys Leu Ile Phe Lys Leu Ser Val Gly
               1           5                      10

ATA ACT CCT CTT GCC TTA ATC GGT TTA GGT AGT TTT GGA TTA GCA      790
Ile Thr Pro Leu Ala Leu Ile Gly Leu Gly Ser Phe Gly Leu Ala
 15              20                  25

GTT TCT GGA GCT AAG CCA AAT AAC CTT AAA CCT GTT AAC CAA GTT      835
Val Ser Gly Ala Lys Pro Asn Asn Leu Lys Pro Val Asn Gln Val
 30              35                  40

GGG GAA ATG AAT TCA CAA GGT CAA TCT AAT CTT TTA GAG AAA GCA      880
Gly Glu Met Asn Ser Gln Gly Gln Ser Asn Leu Leu Glu Lys Ala
 45              50                  55

CGT AGA TGA AGA AAC TCT AAC TTC ACA TCA CTT TCA ATT GAC GGC      925
Arg Arg Trp Arg Asn Ser Asn Phe Thr Ser Leu Ser Ile Asp Gly
 60              65                  70

ACC AAC CCA GGT GCA TTA GTT TTA ACT GGA TCA AAA TCA ATT AGC      970
Thr Asn Pro Gly Ala Leu Val Leu Thr Gly Ser Lys Ser Ile Ser
 75              80                  85

CGG ATT GAT TTG TAT GGT AAC GTG ATT TGA ACG TTT GAT CCA GGT     1015
Arg Ile Asp Leu Tyr Gly Asn Val Ile Trp Thr Phe Asp Pro Gly
 90              95                 100

AAT ACA AAC GAT CTA ACT GGT AAG GTT GGA TTT TAT GAT GCT AAC     1060
Asn Thr Asn Asp Leu Thr Gly Lys Val Gly Phe Tyr Asp Ala Asn
105             110                 115

AAT AAA TTG ACT GCA TTT TCT GGA GAC GTT TCT TTT AAT GTA AGT     1105
Asn Lys Leu Thr Ala Phe Ser Gly Asp Val Ser Phe Asn Val Ser
120             125                 130

GAT CTA AGC TCT AAA ACA GTT GTA GAA GCT ACT CAA GAT CAA GAA     1150
Asp Leu Ser Ser Lys Thr Val Val Glu Ala Thr Gln Asp Gln Glu
135             140                 145

GAT CCT AAT GTT TTC TAC TTA TTA TTA ATG CCA GAT GCA GCG GTT     1195
Asp Pro Asn Val Phe Tyr Leu Leu Leu Met Pro Asp Ala Ala Val
150             155                 160

CAA CAA GAA CAA AAG ACT AAA GAT CAA GTG TTT GAA AAC TAC TTT     1240
Gln Gln Glu Gln Lys Thr Lys Asp Gln Val Phe Glu Asn Tyr Phe
165             170                 175

ATG TCT GAT GCA CCT GCT GCT GGT GAT ACT AGC GCT GAA GGT TCT     1285
Met Ser Asp Ala Pro Ala Ala Gly Asp Thr Ser Ala Glu Gly Ser
180             185                 190

GCA ACT CCT GCT GGT GGT GGT TCA GGT AGT AGT GCT GCT GGA GGA     1330
Ala Thr Pro Ala Gly Gly Gly Ser Gly Ser Ser Ala Ala Gly Gly
195             200                 205

GGT GCT GTT GCT CCT GCT GCA GCC AGT TCG ACT GCT AGA CTT GTT     1375
Gly Ala Val Ala Pro Ala Ala Ala Ser Ser Thr Ala Arg Leu Val
210             215                 220

GAA GAA GGG AAT AGT GCC GGT ATG GGA ACG ATG ACT CCT ACT GCT     1420
Glu Glu Gly Asn Ser Ala Gly Met Gly Thr Met Thr Pro Thr Ala
225             230                 235

TCT ACT TCT GAA ACA GTT ATA GAT TAT AAT AGC GAT CAA AAT AAA     1465
Ser Thr Ser Glu Thr Val Ile Asp Tyr Asn Ser Asp Gln Asn Lys
240             245                 250

ATT CCT AAA CCT AAA ACA CTA TTA GAC AGT AGC GAA AGT TCT GAA     1510
Ile Pro Lys Pro Lys Thr Leu Leu Asp Ser Ser Glu Ser Ser Glu
```

| | | | | | | | | | | |
|---|---|---|---|---|---|---|---|---|---|---|
| 255 | | | | 260 | | | | 265 | | |
| AGT | ATC | AAT | GGT | GGA | AGA | ACA | TAT | GCG | AAT | ATT | AAC | ACT | CAG | AAG | 1555 |
| Ser | Ile | Asn | Gly | Gly | Arg | Thr | Tyr | Ala | Asn | Ile | Asn | Thr | Gln | Lys | |
| 270 | | | | | 275 | | | | 280 | | | | | | |

AAT TTA CAA GGT GTT ATT GTA AAA GTT AAC GAA AAT TTA TTT AAT    1600
Asn Lys Gln Gly Val Ile Val Lys Val Asn Glu Asn Lys Phe Asn
285                 290                 295

TCA GAA AAC CCC TTT GCA GTA GAA AAT ATG GCG TTC ATT AAG CCG    1645
Ser Glu Asn Pro Phe Ala Val Glu Asn Met Ala Phe Ile Lys Pro
300                 305                 310

AAG GAT ATG GTT GAT AAT TAT CCT TCT ACT TGA ACA CAA GGT TCT    1690
Lys Asp Met Val Asp Asn Tyr Pro Ser Thr Trp Thr Gln Gly Ser
315                 320                 325

GCT AAC GGT AAA ATG ACT AAC GTT CTT CAA TTC TAC AAA CAT GAT    1735
Ala Asn Gly Lys Met Thr Asn Val Lys Gln Phe Tyr Lys His Asp
330                 335                 340

AAT CCT AAT GCT GTT AAC AAT AGA TTC TAT AGA GCA AAA TAC TAT    1780
Asn Pro Asn Ala Val Asn Asn Arg Phe Tyr Arg Ala Lys Tyr Tyr
345                 350                 355

CCT AAA CGT TTA GAA ACT CAA ACA ACT ACT CCT CTA ATT GAT AGT    1825
Pro Lys Arg Leu Glu Thr Gln Thr Thr Thr Pro Leu Ile Asp Ser
360                 365                 370

TCT TTC TCT CCA TAT GAG CAT CCA GAA TGA TAT GAA GGT AAT CAA    1870
Ser Phe Ser Pro Tyr Glu His Pro Glu Trp Tyr Glu Gly Asn Gln
375                 380                 385

TTT GTA ATG CCG TGA ATG CAG TAC ATA ACA AAT TTA GGT GGT TTA    1915
Phe Val Met Pro Trp Met Gln Tyr Ile Thr Asn Lys Gly Gly Leu
390                 395                 400

TAT GCT AAA GAT GGA ATG GTG TAC CTA TTT GGT GGT AAC GGT ACA    1960
Tyr Ala Lys Asp Gly Met Val Tyr Leu Phe Gly Gly Asn Gly Thr
405                 410                 415

TGA GTT AAC AAC GAA AGT GCA TTA AGT ATT GGT GTT TTC AGA ACT    2005
Trp Val Asn Asn Glu Ser Ala Leu Ser Ile Gly Val Phe Arg Thr
420                 425                 430

AAA TTT GAA AAC AGA ACT GCT GAA GCT CCA GGA AAC ACT AAA ACT    2050
Lys Phe Glu Asn Arg Thr Ala Glu Ala Pro Gly Asa Thr Lys Thr
435                 440                 445

GTT GGT TAT CCA TAC GGT ATT TTA TTA TCA GCG ATT TCT TTT GAT    2095
Val Gly Tyr Pro Tyr Gly Ile Leu Leu Ser Ala Ile Ser Phe Asp
450                 455                 460

GCT ACT AGA AAT GGA TTA GCA CTT GCT GCT CCT GCA CTT GGT CAA    2140
Ala Thr Arg Asn Gly Leu Ala Leu Ala Ala Pro Ala Lys Gly Gln
465                 470                 475

GAT GTT GGT TAT CAC TTT GTT CCT CGT CTT GCA GTG GGT GGT GTA    2185
Asp Val Gly Tyr His Phe Val Pro Arg Leu Ala Val Gly Gly Val
480                 485                 490

AGT TCA CCT AGA GGA GCT AAC GGT AAT ATT TTC TTA GGT TCA GCT    2230
Ser Ser Pro Arg Gly Ala Asn Gly Asn Ile Phe Leu Gly Ser Ala
495                 500                 505

ATT ACT TGA GGA ACA AAC GGT GGT AAT TTC TTA GAT ACT AAA TGA    2275
Ile Thr Trp Gly Thr Asn Gly Gly Asn Phe Leu Asp Thr Lys Trp
510                 515                 520

CAC AGT CCA GCC GTT ATT GAA GAT GCA ·CCT ACA ACT TTT ATA ACT    2320
His Ser Pro Ala Val Ile Glu Asp Ala Pro Thr Thr Phe Ile Thr
525                 530                 535

GTT AAT AGT AGT GGT GTG CTT CAG AAT AGT GGA AGT CAA CAA TCA    2365
Val Asn Ser Ser Gly Val Leu Gln Asn Ser Gly Ser Gln Gln Ser
540                 545                 550

ACT TCT ACT CCG ATG CCT AAT AGT AAC GGT AAT GAA AGC ATC CCT    2410
Thr Ser Thr Pro Met Pro Asn Ser Asn Gly Asn Glu Ser Ile Pro
555                 560                 565

| | | | | | | | | | | | | | | | |
|---|---|---|---|---|---|---|---|---|---|---|---|---|---|---|---|
| TAT | AGA | TGA | ACG | AAT | TCT | TAT | GAT | TAC | AAC | TCT | GTA | AGA | TTT | GCA | 2455 |
| Tyr | Arg | Trp | Thr | Asn | Ser | Tyr | Asp | Tyr | Asn | Ser | Val | Arg | Phe | Ala | |
| 570 | | | | | 575 | | | | 580 | | | | | | |
| GCT | CTA | ATT | AGT | AAG | CCA | GCT | GGT | GGA | AAC | ACA | AAA | CAA | GTT | GAA | 2500 |
| Ala | Leu | Ile | Ser | Lys | Pro | Ala | Gly | Gly | Asn | Thr | Lys | Gln | Val | Glu | |
| 585 | | | | | 590 | | | | | 595 | | | | | |
| TCA | TTA | TTT | ACA | ACC | GCT | TTA | AAA | TTA | GAT | ACA | TTA | AAT | TCT | TTA | 2545 |
| Ser | Leu | Phe | Thr | Thr | Ala | Leu | Lys | Leu | Asp | Thr | Leu | Asn | Ser | Leu | |
| 600 | | | | | 605 | | | | | 610 | | | | | |
| CCA | AAT | AAA | TTT | ACT | CAA | GAA | AAT | AAT | ATC | TTC | TTT | AGT | TAT | GCT | 2590 |
| Pro | Asn | Lys | Phe | Thr | Gln | Glu | Asn | Asn | Ile | Phe | Phe | Ser | Tyr | Ala | |
| 615 | | | | | 620 | | | | | 625 | | | | | |
| ATG | TTA | GAT | GGT | CGT | CAA | TGA | AGT | TTA | GGT | ACA | CGA | AAA | GAC | AGC | 2635 |
| Met | Leu | Asp | Gly | Arg | Gln | Trp | Ser | Leu | Gly | Thr | Arg | Lys | Asp | Ser | |
| 630 | | | | | 635 | | | | | 640 | | | | | |
| ACA | TGA | TTA | ACA | ACT | AAT | ACT | ATT | AAT | AAC | TTC | ACT | TAT | AAT | ACA | 2680 |
| Thr | Trp | Leu | Thr | Thr | Asn | Thr | Ile | Asn | Asn | Phe | Thr | Tyr | Asn | Thr | |
| 645 | | | | | 650 | | | | | 655 | | | | | |
| CAA | CAA | CAA | TTA | GCG | TCT | ACA | GCA | GCA | GGA | GAA | AAC | GCT | AAT | CCA | 2725 |
| Gln | Gln | Gln | Leu | Ala | Ser | Thr | Ala | Ala | Gly | Glu | Asn | Ala | Asn | Pro | |
| 660 | | | | | 665 | | | | | 670 | | | | | |
| AGA | AAT | ATC | TTA | AAC | GCT | TTA | ACA | ACT | GCA | AAA | GGG | TTT | GAT | CGA | 2770 |
| Arg | Asn | Ile | Leu | Asn | Ala | Leu | Thr | Thr | Ala | Lys | Gly | Phe | Asp | Arg | |
| 675 | | | | | 680 | | | | | 685 | | | | | |
| AGA | GAT | ATT | GGT | AAT | GTA | GAT | ATA | CTA | TAT | TCT | AAT | AAT | ACT | AAT | 2815 |
| Arg | Asp | Ile | Gly | Asn | Val | Asp | Ile | Leu | Tyr | Ser | Asn | Asn | Thr | Asn | |
| 690 | | | | | 695 | | | | | 700 | | | | | |
| AAG | TTT | ACT | TAT | TAC | TAT | CAA | GTT | GGT | GGC | GCG | ATT | ACA | ACT | TGA | 2860 |
| Lys | Phe | Thr | Tyr | Tyr | Tyr | Gln | Val | Gly | Gly | Ala | Ile | Thr | Thr | Trp | |
| 705 | | | | | 710 | | | | | 715 | | | | | |
| CCA | GAA | GTT | CAA | GTA | AAT | TAC | AAA | ACT | TCG | GCT | AAT | ATT | ACT | TAC | 2905 |
| Pro | Glu | Val | Gln | Val | Asn | Tyr | Lys | Thr | Ser | Ala | Asn | Ile | Thr | Tyr | |
| 720 | | | | | 725 | | | | | 730 | | | | | |
| TAC | AAT | TTA | ACT | AGA | ACT | GAT | TTT | GGA | AGT | ACT | ACT | CCT | GCA | ACT | 2950 |
| Tyr | Asn | Leu | Thr | Arg | Thr | Asp | Phe | Gly | Ser | Thr | Thr | Pro | Ala | Thr | |
| 735 | | | | | 740 | | | | | 745 | | | | | |
| CAA | GAT | GCA | AAT | ACC | GTA | TCA | TCT | AAA | TTA | AAC | GGC | GCT | TAC | TTA | 2995 |
| Gln | Asp | Ala | Asn | Thr | Val | Ser | Ser | Lys | Leu | Asn | Gly | Ala | Tyr | Leu | |
| 750 | | | | | 755 | | | | | 760 | | | | | |
| TCA | TCA | ACT | GGC | GAT | CAA | CAA | GGA | TGA | TAC | AAC | GGT | TCA | ATC | TAT | 3040 |
| Ser | Ser | Thr | Gly | Asp | Gln | Gln | Gly | Trp | Tyr | Asn | Gly | Ser | Ile | Tyr | |
| 765 | | | | | 770 | | | | | 775 | | | | | |
| GTT | AAA | AAA | GCG | AGC | TTT | ACA | CCA | AGT | AGT | CAA | GGT | TAT | ACT | TGA | 3085 |
| Val | Lys | Lys | Ala | Ser | Phe | Thr | Pro | Ser | Ser | Gln | Gly | Tyr | Thr | Trp | |
| 780 | | | | | 785 | | | | | 790 | | | | | |
| CAA | GAT | TTC | AAA | GGT | TTA | ACA | ACT | ACA | GCA | AGT | AAC | GCA | GTT | ATT | 3131 |
| Gln | Asp | Phe | Lys | Gly | Leu | Thr | Thr | Thr | Ala | Ser | Asn | Ala | Val | Ile | |
| 795 | | | | | 800 | | | | | 805 | | | | | |
| TCT | AAC | TGA | ACA | AAA | GCT | GGA | TAC | AGT | ATT | AGA | CCA | GAT | GAT | GAT | 3175 |
| Ser | Asn | Trp | Thr | Lys | Ala | Gly | Tyr | Ser | Ile | Arg | Pro | Asp | Asp | Asp | |
| 810 | | | | | 815 | | | | | 820 | | | | | |
| ACA | GTA | TTC | AGC | GTT | TCT | AAG | ATT | CCT | TTT | GAA | AAA | GAA | ATT | ACT | 3220 |
| Thr | Val | Phe | Ser | Val | Ser | Lys | Ile | Pro | Phe | Glu | Lys | Glu | Ile | Thr | |
| 825 | | | | | 830 | | | | | 835 | | | | | |
| GCT | GCT | GTT | AAT | GTA | AGA | TCA | TTA | GAT | AGT | TAC | TAT | GTA | CAA | TTA | 3265 |
| Ala | Ala | Val | Asn | Val | Arg | Ser | Leu | Asp | Ser | Tyr | Tyr | Val | Gln | Leu | |
| 840 | | | | | 845 | | | | | 850 | | | | | |
| AAT | GGT | GAA | ACT | TCA | GTT | AAT | ACT | GTA | GCT | AGA | GTA | AGT | CCT | GAT | 3310 |
| Asn | Gly | Glu | Thr | Ser | Val | Asn | Thr | Val | Ala | Arg | Val | Ser | Pro | Asp | |
| 855 | | | | | 860 | | | | | 865 | | | | | |
| TCT | AGC | GCT | TTA | ACC | CTA | AAC | CCT | AAA | CGA | ATT | ACT | AAC | CCA | TTG | 3355 |
| Ser | Ser | Ala | Leu | Thr | Leu | Asn | Pro | Lys | Arg | Ile | Thr | Asn | Pro | Leu | |

| | | | | | | | | | | | | | | |
|---|---|---|---|---|---|---|---|---|---|---|---|---|---|---|
| 870 | | | | | 875 | | | | | 880 | | | | |
| ATG | AAT | AGA | GAT | AAT | GTA | ATC | GGT | CAA | GGT | GCT | TTC | ATT | AGT | AGA |
| Met | Asn | Arg | Asp | Asn | Val | Ile | Gly | Gln | Gly | Ala | Phe | Ile | Ser | Arg |
| 885 | | | | | 890 | | | | | 895 | | | | |

3400

| AAT | GAT | ATT | CCA | TCA | TCA | TTC | TTT | GAA | AAC | AAA | ATT | AAT | GAT | ATT |
|---|---|---|---|---|---|---|---|---|---|---|---|---|---|---|
| Asn | Asp | Ile | Pro | Ser | Ser | Phe | Phe | Glu | Asn | Lys | Ile | Asn | Asp | Ile |
| 900 | | | | | 905 | | | | | 910 | | | | |

3445

| GTA | ACT | ACA | GAA | GCT | GAT | GGT | ACA | GAA | GTA | TTA | GAT | AGT | AAA | TAC |
|---|---|---|---|---|---|---|---|---|---|---|---|---|---|---|
| Val | Thr | Thr | Glu | Ala | Asp | Gly | Thr | Glu | Val | Leu | Asp | Ser | Lys | Tyr |
| 915 | | | | | 920 | | | | | 925 | | | | |

3490

| ATT | AAT | TCA | ATT | TAC | AGA | TAT | ACT | CCA | CCT | CAA | AAC | AAT | CCT | CAT |
|---|---|---|---|---|---|---|---|---|---|---|---|---|---|---|
| Ile | Asn | Ser | Ile | Tyr | Arg | Tyr | Thr | Pro | Pro | Gln | Asn | Asn | Pro | His |
| 930 | | | | | 935 | | | | | 940 | | | | |

3535

| ATT | AGA | TTA | AGA | TTA | TTA | GTA | ATT | GAT | CGT | TCT | AGA | GCA | ACC | AAT |
|---|---|---|---|---|---|---|---|---|---|---|---|---|---|---|
| Ile | Arg | Leu | Arg | Leu | Leu | Val | Ile | Asp | Arg | Ser | Arg | Ala | Thr | Asn |
| 945 | | | | | 950 | | | | | 955 | | | | |

3580

| GAC | TTC | ATT | AAG | TTA | TTA | CCT | CAA | GTA | TTA | GTT | GAT | GGC | GAA | TAC |
|---|---|---|---|---|---|---|---|---|---|---|---|---|---|---|
| Asp | Phe | Ile | Lys | Leu | Leu | Pro | Gln | Val | Leu | Val | Asp | Gly | Glu | Tyr |
| 960 | | | | | 965 | | | | | 970 | | | | |

3625

| GTT | GCT | GTT | CCA | CAA | GCT | AAT | AGT | GTG | TTT | GTG | TCT | GAC | CAA | GAA |
|---|---|---|---|---|---|---|---|---|---|---|---|---|---|---|
| Val | Ala | Val | Pro | Gln | Ala | Asn | Ser | Val | Phe | Val | Ser | Asp | Gln | Glu |
| 975 | | | | | 980 | | | | | 985 | | | | |

3670

| TTT | ACT | GGT | TTT | GAT | GCT | CTT | CCA | GGT | TAT | GTA | TTA | CCA | GTA | GCG |
|---|---|---|---|---|---|---|---|---|---|---|---|---|---|---|
| Phe | Thr | Gly | Phe | Asp | Ala | Leu | Pro | Gly | Tyr | Val | Leu | Pro | Val | Ala |
| 990 | | | | | 995 | | | | | 1000 | | | | |

3715

| ATC | TCG | ATT | CCG | ATC | ATC | ATA | ATT | GCC | TTG | GCA | TTA | GCT | TTA | GGT |
|---|---|---|---|---|---|---|---|---|---|---|---|---|---|---|
| Ile | Ser | Ile | Pro | Ile | Ile | Ile | Ile | Ala | Leu | Ala | Leu | Ala | Leu | Gly |
| 1005 | | | | | 1010 | | | | | 1015 | | | | |

3760

| CTA | GGT | ATT | GGT | ATT | CCA | ATG | TCT | CAA | AAC | CGT | AAG | ATG | TTG | AAG |
|---|---|---|---|---|---|---|---|---|---|---|---|---|---|---|
| Leu | Gly | Ile | Gly | Ile | Pro | Met | Ser | Gln | Asn | Arg | Lys | Met | Leu | Lys |
| 1020 | | | | | 1025 | | | | | 1030 | | | | |

3805

| CAA | GGA | TTT | GCG | ATT | TCA | AAC | AAA | AAA | GTT | GAT | ATT | CTG | ACA | ACA |
|---|---|---|---|---|---|---|---|---|---|---|---|---|---|---|
| Gln | Gly | Phe | Ala | Ile | Ser | Asn | Lys | Lys | Val | Asp | Ile | Leu | Thr | Thr |
| 1035 | | | | | 1040 | | | | | 1045 | | | | |

3850

| GCC | GTT | GGT | AGT | GTG | TTC | AAA | CAA | ATT | ATT | AAT | CGA | ACA | TCT | GTG |
|---|---|---|---|---|---|---|---|---|---|---|---|---|---|---|
| Ala | Val | Gly | Ser | Val | Phe | Lys | Gln | Ile | Ile | Asn | Arg | Thr | Ser | Val |
| 1050 | | | | | 1055 | | | | | 1060 | | | | |

3895

| ACA | AAT | ATT | AAG | AAG | ACT | CCA | CAA | ATG | CTT | CAA | GCC | AAC | AAG | AAA |
|---|---|---|---|---|---|---|---|---|---|---|---|---|---|---|
| Thr | Asn | Ile | Lys | Lys | Thr | Pro | Gln | Met | Leu | Gln | Ala | Asn | Lys | Lys |
| 1065 | | | | | 1070 | | | | | 1075 | | | | |

3940

| GAT | GGA | GCA | TCT | TCA | CCA | AGC | AAG | CCA | TCA | GCT | CCA | GCT | GCT | AAG |
|---|---|---|---|---|---|---|---|---|---|---|---|---|---|---|
| Asp | Gly | Ala | Ser | Ser | Pro | Ser | Lys | Pro | Ser | Ala | Pro | Ala | Ala | Lys |
| 1080 | | | | | 1085 | | | | | 1090 | | | | |

3985

| AAA | CCA | ACA | GGA | CCA | ACT | AAA | CCA | TCT | GCT | CCA | GGA | GCA | AAA | CCA |
|---|---|---|---|---|---|---|---|---|---|---|---|---|---|---|
| Lys | Pro | Thr | Gly | Pro | Thr | Lys | Pro | Ser | Ala | Pro | Gly | Ala | Lys | Pro |
| 1095 | | | | | 1100 | | | | | 1105 | | | | |

4030

| ACA | GCA | CCA | GCT | AAA | CCA | AAA | GCT | CCA | GCA | CCA | ACT | AAG | AAA | ATT |
|---|---|---|---|---|---|---|---|---|---|---|---|---|---|---|
| Thr | Ala | Pro | Ala | Lys | Pro | Lys | Ala | Pro | Ala | Pro | Thr | Lys | Lys | Ile |
| 1110 | | | | | 1115 | | | | | 1120 | | | | |

4075

GAA TAATTAAGGT AATATATTAA AGATATGAAT ATTTCTAAAA AACTTAAAAG    4128
Glu
1122

TTATACATTG ATAGGTGGAT TAGCTGTATT TGGAACTCTT GGTTCTGCAA GCTT    4182

GENE ENCODING CYTADHESIN PROTEIN OF MYCOPLASMA GALLISEPTICUM AND ITS USE

FIELD OF THE INVENTION

The invention relates to the field of molecular biology, and more particularly, to the isolation, cloning and use of a nucleic acid sequence encoding a cytadhesin protein of *Mycoplasma gallisepticum*.

BACKGROUND OF THE INVENTION

*Mycoplasma gallisepticum* is a pathogen of the avian respiratory tract. Sporadic outbreaks, having important economic consequences, occur in turkeys and broiler chickens, and remain a costly enzootic infection in commercial egg layers. The cytadhesin protein of the organism is a virulence determinant involved in the attachment of the organism to host surfaces during infection via recognition of host receptors.

In current practice, prophylactic immunization of fowl against *M. gallisepticum* related disease involves either controlled exposure to attenuated vaccine strains (for example the "F strain"), or the use of inactivated, whole cell oil emulsion vaccines. Each of these approaches has certain disadvantages. For example, live vaccines can produce disease or impair reproductive function. Inactivated vaccines, while generally effective in preventing disease in immunized birds, do not reliably prevent infection, and may allow spread of infection and disease to unvaccinated birds.

Improvements are also needed in current diagnostic tests for the presence of *M. gallisepticum* in fowl. Current methods for diagnosis of *M. gallisepticum* infections by serological methods typically employs whole organisms to assay the presence of antibodies against *M. gallisepticum*. These tests are costly and time consuming, and can produce false positive or false negative results due to nonspecific reactions.

U.S. Pat. No. 5,026,636, issued Jun. 25, 1991, discloses the isolation of the P1 cyadhesion gene from *M. pneumoniae*. U.S. Pat. No. 5,158,870, issued Oct. 27, 1992, discloses diagnosis of *M. genitalium* infection using monoclonal antibodies.

SUMMARY OF THE INVENTION

The invention relates to isolated and substantially purified nucleic acid molecules encoding the *M. gallisepticum* cytadhesin protein. While it has not been conclusively established that the product encoded by the nucleic acid of the invention is a cytadhesin protein, strong evidence has been found suggesting that the encoded product is homologous to, although considerably different from, the cytadhesins of human mycoplasmas. Accordingly, the presumptive cytadhesin product will be referred to herein as "cytadhesin". The invention further relates to use of the disclosed nucleic acid, and polypeptide expression products thereof, in immunoprophylactic immunization of fowl and as a diagnostic reagent.

DESCRIPTION OF THE PREFERRED EMBODIMENTS

Figure 1:
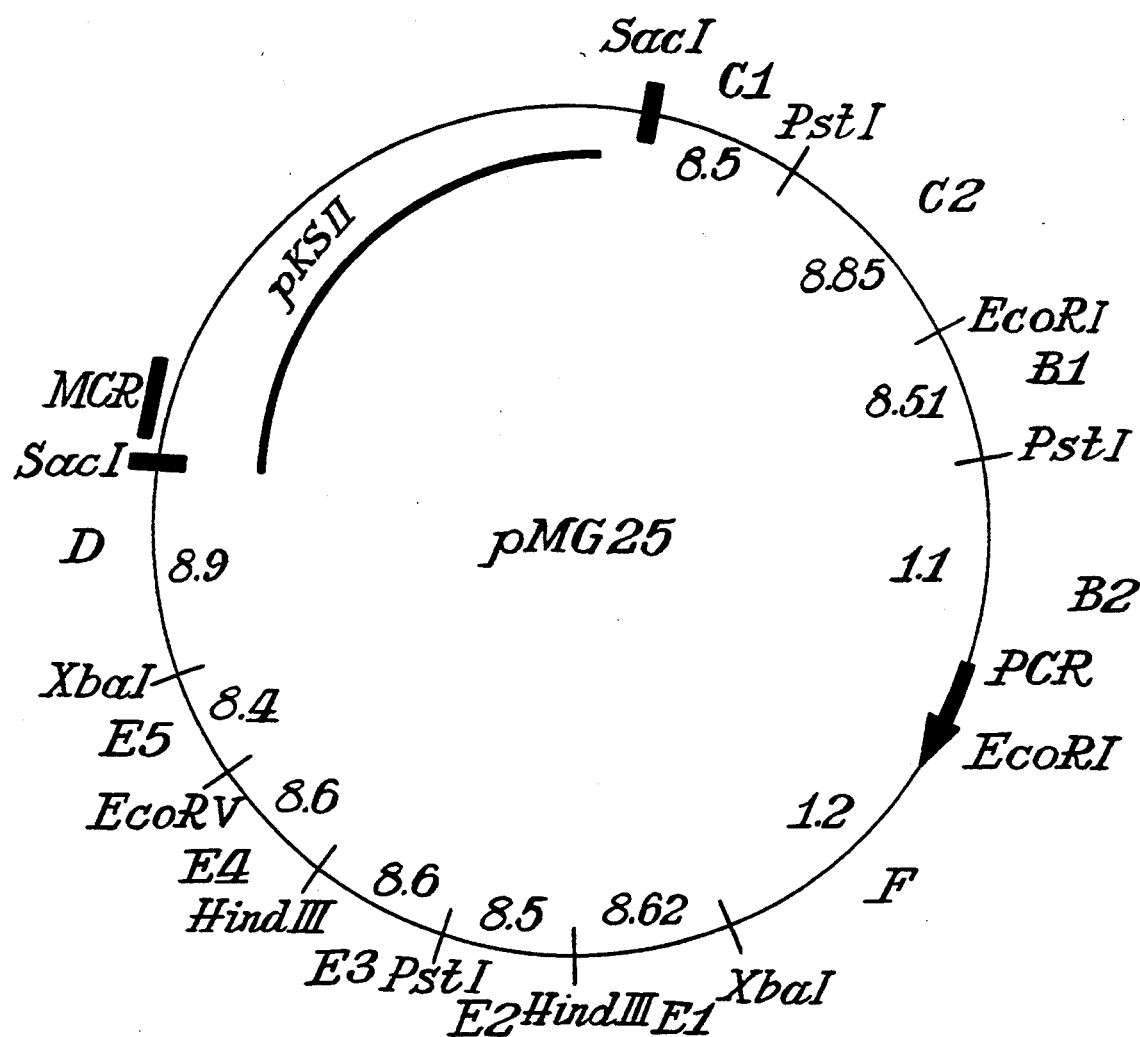
FIG. 1 is a schematic drawing of the plasmid pMG25, which contains the 8.0 kb SacI fragment, described more fully in Example 1. The position of the vector pKSII sequence with the plasmid is shown, and the position of the PCR fragment within the genomic DNA insert is shown. MCR designates a multiple cloning region.

The nucleic acid sequence of the *M. gallisepticum* cytadhesin gene in accordance with the invention, and the amino acid sequence of the protein imputed therefrom, is shown in the appended SEQ ID NO: 1. In addition to the specific sequence presented, those skilled in the art would be enabled by the sequence data provided herein to isolate allelic forms of the gene from other *M. gallisepticum* strains. As disclosed in the following examples, the disclosed sequence was isolated from strain S6, a widely available research strain of *M. gallisepticum*. It is also contemplated that fragments or sequence variants of the full length nucleic acid sequence would have utility in certain aspects of the invention, as described more fully below.

The gene may be obtained by isolation from *M. gallisepticum* genomic DNA. For example, using the sequence data provided herein, highly specific probes or PCR primers can be designed which enable isolation of the gene from a genomic digest or library of *M. gallisepticum* DNA. Probing and PCR techniques for carrying out the isolation are known in the art. PCR techniques are disclosed, for example, in U.S. Pat. Nos. 4,683,202, 4,683,195, and 4,889,818. An amplified PCR fragment provides a suitable probe to obtain full-length clones from a library or genomic digest of *M. gallisepticum* DNA. The isolated gene may then be propogated and amplified to useful quantities by conventional cloning methodology, for example in a plasmid or phage vector transformed into an *E. coli* host.

As more fully described in the examples which follow, the gene was initially isolated from *M. gallisepticum* S6 strain by the use of PCR primers based on sequences which are conserved in two heterologous human mycoplasma species, namely *M. pneumoniae* and *M. genitalium*, the sequences of which have been previously characterized. These human mycoplasmas have homology in the respective cytadhesin proteins designated P1 and MgPa, respectively. See Dallo et al., Inf. and Imm. 57: 1059 (1989); Inamine et al., Gene 82: 259 (1989). As will be understood to those skilled in the art, the sequence data derived from strain S6 and presented herein will enable isolation and detection of homologous DNA from other *M. gallisepticum* strains. Use as a probe may enable isolation and detection of redundant copies of the gene or portions thereof which may occur in the *M. gallisepticum* genome, or other portions of the attachment operon.

The nucleic acid sequence of the invention is preferably DNA. The DNA sequence of the invention or particular fragments thereof can be expressed in vitro into recombinant polypeptide using known and commercially available expression systems. For example, the entire gene sequence, or a fragment thereof, may be incorporated into an expression vector under transcriptional control of elements regulating transcription. Depending on the vector, the product may be expressed as a fusion product. Preferred fragments are about 30 to 600 nucleotides in length, but may be up to 2 kb in size. Since UGA encodes tryptophan in mycoplasma but acts as a universal stop codon in other systems, the fragment is preferably free or substantially free of UGA codons, at least in the 5 prime portion of the fragment being expressed. This can be assured by either inspection of the sequence to select a UGA-free portion, or by altering the sequence by site-directed mutagenesis to delete those codons. Fragments of the full length nucleic acid may be generated in conventional manner, using restriction enzymes or mechanical shearing, or may be synthesized synthetically. Optionally the fragments may be further treated by blunt ending, addition of linkers, or the like, to facilitate insertion into a cloning vehicle or expression vector. It is currently considered that expression of particular fragments of the gene will be of more significance than expression of a full-length polypeptide. It is likely that only certain epitopes of the full length protein in its native conformation are either immunologically accessible or strongly immunogenic. It is possible that certain important domains could be identified by analysis of the sequence data itself. Important fragments or epitopes can be identified by screening procedures known in the art. For example, anti-cytadhesin antibodies could be used as an immunological reagent to screen a λgt11 expression library of gene fragments. Certain monoclonal antibodies have been characterized which interfere with or block the cytadhesion event, and such antibodies would be suitable for use in screening for fragments expressing antigenic epitopes. Also, as is known to those skilled in the art, full-length mycoplasma sequences can be difficult to express in vitro due to irregular codon usage. Accordingly, a particularly preferred use of the gene sequence is to express fragments of the sequence encoding immunogenic epitopes of the cytadhesin protein. Techniques for in vitro expression to produce recombinant polypeptide, including vector construction, transformation of hosts, expression, and recovery of recombinant protein, are known in the art and are not described in detail. Reference is made to the following sources for exemplary disclosure: Maniatis et al., Molecular Cloning: A Laboratory Manual, Cold Spring Harbor Laboratory (1982); Berger and Kimmel, Guide to Molecular Cloning Techniques, Methods in Enzymology, Vol. 152 (1987); Ausubel et al., Current Protocols in Molecular Biology, New York: Green Publishing/Wiley Interscience (1989); Sambrook et al., Molecular Cloning: A Laboratory Manual, Cold Spring Harbor Laboratory (1989); U.S. Pat. No. 5,026,636, and references cited therein. Expression in vivo in a bacterial vector or a viral vector, such as fowlpox, is also contemplated. See, for example, Finkelstein and Silva, Trends in Biotechnology 7: 273 (1989).

The recombinant polypeptide or polypeptide fragment obtained as described above may be used in various immunoassay formats to assay for anti-*M. gallisepticum* antibodies in samples, such as serological samples from poultry, as an indicia of infection. Any conventional immunoassay formats, such as liquid phase or solid phase, are suitable. For example, the polypeptide or fragment may be affixed to a solid phase and contacted with a sample suspected of containing anti-*M. gallisepticum* antibodies, the sample being obtained from a bird suspected of being infected with *M. gallisepticum*. Immunoassay and diagnostic formats for determining the presence or amount of an analyte are known, and can be practiced using the polypeptides or polypeptide fragments of the invention as a reagent. It is also contemplated that the recombinant polypeptide or fragments can be used to generate anti-*M. gallisepticum* antibodies which are themselves useful as immunoassay reagents. Moreover, the sequence information presented herein derived from strain S6 may allow generation of *M. gallisepticum* cytadhesin peptide fragments which are uniquely specific for the virulent strains of *M. gallisepticum*. In the context of diagnostic tests, the unique specificity of the reagents to *M. gallisepticum* will reduce or eliminate the false positives which occur in the current serological test formats due to nonspecific reaction with other mycoplasma organisms.

A further utility of the nucleic acid sequence of the invention, or nucleic acid complementary in sequence thereto, is use as a diagnostic probe for the presence of *M. gallisepticum* DNA in a sample or the identification of *M. gallisepticum* DNA. As shown in the following examples, certain nucleic acid fragments of the invention are capable of reacting specifically with *M. gallisepticum* DNA but not with the DNA of other mycoplasma species. Current nucleic acid probes for *M. gallisepticum* are based on unidentified portions of the genome.

Use of the sequence as an probe can involve detection of *M. gallisepticum* in a sample. For example, a swab sample from a bird suspected of being infected may be subjected to PCR amplification or hybridization analysis to detect the presence of *M. gallisepticum* DNA in the sample. Some fragments may serve as less specific probes, depending on hybridization conditions.

The cytadhesion polypeptide and fragments of polypeptide expressed from the sequence have potential utility as a component of a subunit vaccine, alone or together with additional vaccine components now in use. Cytadhesions from other organisms are known to be immunogenic. The subunit vaccine, consisting of the polypeptide in a suitable, pharmaceutically acceptable carrier, may have utility in prophylatic protection of fowl from infection by *M. gallisepticum* or prevention of *M. gallisepticum* related disease, free of any risk of spreading infection or disease to uninfected fowl. A similar formulation of peptide in carrier may find utility as an immunomodulator in poultry, for it has been observed that the surface molecules of certain mammalian mycoplasma can modulate cellular and humoral immune responses.

The following examples are provided by way of illustration and not as limiting the scope of the invention.

EXAMPLE 1

Isolation of the Cytadhesin Gene using PCR

The PCR primers were designed to flank a conserved area of the cytadhesin proteins of *M. pnuemoniae* and *M. genitalium*. Based on the observed amino acid homology between these proteins, a pair of degenerate oligonucleotide primers were prepared. The 5' PCR primer was designed degenerately based on nucleotide positions 1211-1229 of the *M. genitalium* cytadhesin sequence disclosed in Dallo et al., Inf. and Imm. 57: 1059 (1989) and nucleotide positions 1309-1328 of the *M. pnuemoniae* cytadhesin sequence disclosed in Su et al., Inf. and Imm. 55: 3023 (1987). The 3' PCR primer was designed degenerately based on nucleotide positions 1780-1796 of the sequence in Dallo et al., supra, and nucleotide positions 1891-1907 of the sequence in Su et al., supra. To the 5 prime end of each primer was added a nine nucleotide sequence containing restriction sites to facilitate cloning. It was predicted that these primers should amplify a fragment of 582-594 base pairs in size.

The degenerate primers were used to initiate PCR on S6 genomic DNA. Genomic DNA from strain S6 was prepared from a 1-liter culture in late log phase as described in Carle et al., DNA Extraction and Purification. In: Methods in Mycoplasmology. Razin and Tully, eds. Academic Press, New York, London (1983). PCR was carried out on genomic S6 DNA using the thermostable DNA polymerase of *T. aquaticus* (Perkin Elmer Cetus Instruments, Norwalk, Conn.) as described in Keeler et al., Avian Dis. 35: 920 (1991). PCR products were analyzed on 1.4% low melting point agarose gels. Products in the 500-600 bp range were cut from gels, purified through NACS columns (BRL Life Technologies, Gaithersburg, Md) and digested with EcoRI and HindIII (New England Biolabs, Beverly, Mass.). The fragments were then cloned into similarly digested plasmid pKSII (Stratagene, La Jolla, Calif.) using molecular cloning techniques described in Ausubel et., supra. Purified double-stranded DNA templates were sequenced with Sequenase II T7 DNA polymerase (United States Biochemical Corp., Cleveland, Ohio) using the dideoxy chain termination method of Sanger et al., PNAS USA 74: 503 (1977).

The above procedure resulted in the isolation of a 578 bp PCR fragment corresponding to nucleotides 1844 to 2422 in SEQ ID NO: 1. The 578 bp fragment was labeled by nick translation and used to probe an *M. gallisepticum* S6 library constructed in the LambdaGEM11 cloning vector. This isolated clone λ4. The 578 bp fragment was found to hybridize to a 1.6 kb EcoRI fragment contained within an 8.0 kb SacI fragment of *M. gallisepticum* DNA from clone λ4. The 8.0 kb SacI fragment was cloned into the plasmid vector pKSII to generate pMG25, which is illustrated in FIG. 1, and was mapped with the restriction enzymes PstI, EcoRI, XbaI, HindIII, and EcoRV. Based on the location of the 1.6 kb EcoRI fragment, five contiguous DNA fragments were subcloned into pKSII: fragment C2 (an 850 bp PstI-EcoRI fragment); fragment B1 (a 510 bp EcoRI-PstI fragment); fragment B2 (an 1100 bp PstI-EcoRI fragment); fragment F (a 1200 bp EcoRI-XbaI fragment); and E1 (a 620 bp XbaI-HindIII fragment). See FIG. 1. These five fragments were sequenced using sequencing primers appropriate for plasmid KSII as well as internal oligonucleotide primers.

Sequence analysis of the 4182 bp of DNA contained within these five fragments identified a 3369 bp open reading frame beginning at nucleotide position 713 and ending at nucleotide position 4081. See SEQ ID NO: 1. The 1122 amino acid protein predicted to be encoded by the open reading frame contains several features which suggest it is a membrane-bound cytadhesin protein. First, it contains a classic N-terminal signal sequence and a potentially membrane-spanning hydrophobic anchor sequence near the carboxy end. Secondly, the protein contains no cysteine residues and the cytoplasmic tail is rich in prolines, both of which features are characteristic of human mycoplasma cytadhesin proteins. The putative *M. gallisepticum* cytadhesin protein shares 28.7% and 26.2% amino acid homology to the *M. pnumoniae* and *M. genitalium* cytadhesin proteins, respectively.

EXAMPLE 2

Expression of a Polypeptide Fragment in *E. coli*

The sequence of the 578 bp PCR fragment of Example 1 was inspected to locate a fragment containing few or no UGA codons, which are universal stop codons which encode tryptophan in mycoplasma. A 391 bp fragment dilineated by two HincII restriction sites was identified which contained only two UGA codons, located 272 and 308 bp downstream of the upstream HincII site. Thus, the 5' portion of this fragment was free of UGA codons, and at least a 90 amino acid fragment encoded by positions 1967 to 2236 on SEQ ID NO: 1 should be expressed without termination in *E. coli*. The pKSII plasmid of Example 1 was cut with HincII and separated on 0.8% agarose gel to yield the 391 bp HincII fragment, which corresponds to nucleotide positions 1967 to 2357 of the sequence shown in SEQ ID NO: 1.

The 391 bp fragment was blunt-end ligated into the SmaI cloning site of the expression plasmid PGEX-3X (Pharmacia LKB Biotechnology, Piscatahway, N.J.). The expression plasmid was predicted to produce a 37 kD fusion protein linked to glutathione S transferase (GST). *E.coli* strain XL-1 (Promega) was transformed with the recombinant plasmid and plated on LB amp medium. Clones containing the correct insert size were sequenced at the cloning site/insert junction and one clone, designated PGEX-3X-IN, was found to have the insert in the correct orientation and in proper reading frame.

Log phase cultures of *E. coli* transformed with PGEX-3X-IN were induced with 0.1 mM isopropylthio-β-D-galactoside and samples were taken hourly for four hours. Bacteria were prepared for SDS-PAGE on a 6% gel after lysis and boiling, as described in Sambrook et al, supra. Analysis of the gel revealed that PGEX-3X-IN produced high yields of a protein in the 35-40 kD range.

EXAMPLE 3

Generation of anti-*M. gallisepticum* Antibodies

Aggregated fusion protein preparations produced by PGEX-3X-IN (Example 2) were separated on 10% SDS-PAGE gels, and cut from the unstained gels after determining migration distance using molecular weight markers. Gel material, mixed with Friend's adjuvant, was repeatedly injected into rabbits at appropriate intervals. Serum samples taken after the third injection were used to determine whether the antibody was reactive with *M. gallisepticum*. In this assay, whole-cell lysates and membrane fractions of *M. gallisepticum* were prepared as described in Razin, Cell Lysis and Isolation of Membranes. In: Methods in Mycoplasmology, Razin and Tully, eds. Academic Press, N.Y. (1983). Following SDS-PAGE separation on 10% polyacrylamide gels, the proteins were transferred onto nitrocellulose membranes and the immunoblot was developed using a 50-fold dilution of the rabbit antisera. The antisera reacted with an approximately 100–120 kD component of the membrane preparation, indicating that the antibody was reactive with a membrane-bound component of *M. gallisepticum*.

EXAMPLE 4

Use of Nucleic Acid Fragment as Diagnostic Probe

Figure 2:
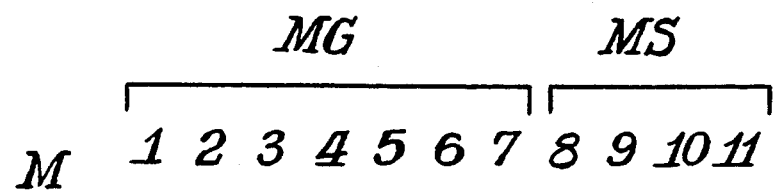
FIG. 2 illustrates distribution of the putative *M. gallisepticum* cytadhesin gene fragment as shown by Southern blotting. Mycoplama DNA (3 μg) was digested with HindIII, electrophoresed on a 0.6% agarose gel, and transferred to a nylon membrane. The membrane was hybridized at high stringency with a $^{32}$-P labeled, 578 bp PCR product (described in the examples). *M. gallisepticum* strains are: S6 (lane 1); R (lane 2); PG31 (lane 3); 1010 (lane 4); F (lane 5); S6 ADH (lane 6); and S6 NA (lane 7). The remaining lanes are *M. synoviae* strains Neb3S (lane 8); F10-2SA (lane 9); 1131 (lane 10); and WVU1853 (lane 11). Derivative strains of S6 designated S6 ADH and S6 NA were derived from strain S6 by selection for glass adherence (ADH) or non-adherence (NA) for 100 passages in Frey broth. Both derivatives were less pathogenic than the parent S6 strain as determined by inoculation of chicken embryo tracheal organ cultures or by inoculation of susceptible chickens and turkeys.
Figure 2:
Figure 3:
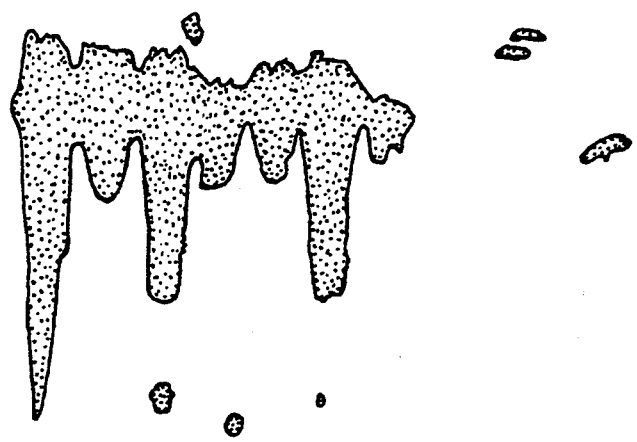
FIG. 3 illustrates the result where the nylon filter of FIG. 2 was stripped of labeled probe and rehybridized using the same probe at low stringency conditions, as described herein. Lane designations are the same as in FIG. 2.
Figure 4:
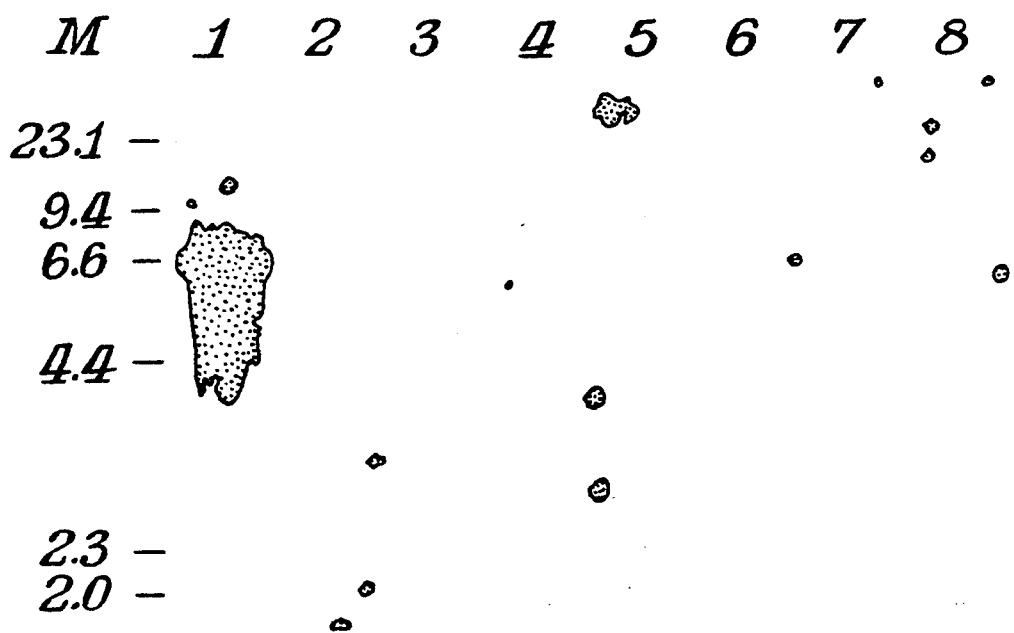
FIG. 4 represents distribution of the putative cytadhesin gene fragment in different mycoplasma species using Southern blotting. Mycoplasma DNA was prepared and transferred to a nylon membrane as described in connection with FIG. 2. The membrane was hybridized with the labeled 578 bp PCR probe (Example 1) at low stringency. Mycoplasma species are as follows: *M. gallisepticum* strain S6 (lane 1); *M. iowae* strain Q (lane 2); *M. iowae* strain R (lane 3); *M. iowae* strain 695 (lane 4); *M. gallinarum* strain 826C2030 (lane 5); *M. meleagridis* (lane 6); *M. genitalium* strain 33530 (lane 7); and *M. pneumoniae* strain 15531 (lane 8).

For use in the following hybridization studies, the results of which are illustrated in FIGS. 2, 3 and 4, the cloned 578 bp PCR fragment (Example 1) was radioactively labeled by nick translation. High and low stringency Southern hybridizations were carried out on various mycoplama DNAs as described in Ausubel et al., supra. Briefly, high-stringency hybridizations were incubated overnight at 42° C. in 50% formamide, followed by two room-temperature washes in 2X SSC (1X SSC contains 0.15M sodium chloride and 0.015M sodium citrate [pH 7]), a 20 minute wash at 65° C. in 2X SSC with 1% SDS and a final 20 minute wash at room temperature in 0.1X SSC. Labeled probe was stripped from nylon membranes by 15 minutes of boiling in 2 liters of 0.1X SSC with 1.0% SDS. Low stringency hybridizations were incubated overnight at 32° C. in 30% formamide. Hybridization was followed by one wash at room temperature in 2X SSC for 10 minutes or by one wash at room temperature followed by one wash for 10 minutes at 65° C. in 2X SSC in 1% SDS.

As seen in FIG. 2, at high stringency the labeled probe detected DNA from *M. gallisepticum* strains S6, R, PG31, 1010, F, S6 ADH, and S6 NA (see lanes 1–7), but did not detect DNA from *M. syvnoviae* strains Neb3S, F10-2SA, 1131, or WVU1853 (see lanes 8–11). Similar results were obtained when the same filter was stripped and rehybridized with the labeled probe at low stringency, as shown in FIG. 3. As seen in FIG. 4, the probe at low stringency discriminated between *M. gallisepticum* DNA (lane 1 and DNA from other mycoplasma species (lanes 2–8). These results illustrate the utility of the nucleic acid sequences of the invention as highly specific diagnostic probes for the detection of *M. gallesepticum* DNA.

---

What is claimed is:

1. An isolated nucleic acid molecule encoding a cytadhesin protein of Mycoplasma gallisepticum having the amino acid sequence of SEQ ID NO: 1.

2. An expression vector comprising the nucleic acid of claim 1.

3. An isolated DNA molecule having the sequence shown in SEQ ID NO: 1 or a sequence fully complementary thereto.

4. An expression vector containing, as insert, the nucleic acid claim 3.

5. A probe for specifically detecting *M. gallisepticum* nucleic acid comprising a nucleic acid molecule corresponding to the contiguous nucleotides of positions 1844 to 2422 of the sequence shown in SEQ ID NO: 1.

6. An expression vector as claimed in claim 4, wherein the nucleic acid is free of UGA codons.

* * * * *